United States Patent
Kitano

(10) Patent No.: US 10,694,119 B2
(45) Date of Patent: Jun. 23, 2020

(54) ENDOSCOPE SYSTEM

(71) Applicant: FUJIFILM Corporation, Tokyo (JP)

(72) Inventor: Ryo Kitano, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/598,337

(22) Filed: Oct. 10, 2019

(65) Prior Publication Data

US 2020/0120288 A1 Apr. 16, 2020

(30) Foreign Application Priority Data

Oct. 11, 2018 (JP) .................. 2018-192464

(51) Int. Cl.
| | | |
|---|---|---|
| *H04N 5/268* | (2006.01) | |
| *A61B 1/05* | (2006.01) | |
| *H04N 5/235* | (2006.01) | |
| *H04N 5/243* | (2006.01) | |
| *H04N 5/262* | (2006.01) | |
| *H04N 5/225* | (2006.01) | |
| *A61B 1/00* | (2006.01) | |

(52) U.S. Cl.
CPC ......... *H04N 5/268* (2013.01); *A61B 1/00006* (2013.01); *A61B 1/00009* (2013.01); *A61B 1/00045* (2013.01); *A61B 1/00177* (2013.01); *A61B 1/00181* (2013.01); *A61B 1/05* (2013.01); *H04N 5/2258* (2013.01); *H04N 5/2351* (2013.01); *H04N 5/243* (2013.01); *H04N 5/2628* (2013.01); *H04N 2005/2255* (2013.01)

(58) Field of Classification Search
CPC ......... H04N 2005/2255; H04N 5/2258; H04N 5/2628; H04N 5/2351; H04N 5/243; H04N 5/268; A61B 1/00177; A61B 1/00009; A61B 1/00045; A61B 1/00006; A61B 1/00181; A61B 1/05
USPC ...... 348/45, 65, 68, 66, 69, 72, 74; 600/101, 600/103, 109, 113, 114, 117, 118, 132, 600/139, 160, 170, 176–178
See application file for complete search history.

(56) References Cited

U.S. PATENT DOCUMENTS

| | | |
|---|---|---|
| 2015/0073218 A1 | 3/2015 | Ito |
| 2015/0265136 A1 | 9/2015 | Honda |
| 2017/0085762 A1 | 3/2017 | Obara et al. |
| 2019/0082085 A1* | 3/2019 | Oka ............... H04N 5/2254 |
| 2019/0110662 A1* | 4/2019 | Obara ............... A61B 1/05 |

FOREIGN PATENT DOCUMENTS

| | | |
|---|---|---|
| JP | 5583873 B1 | 9/2014 |
| JP | 5698879 B2 | 4/2015 |
| JP | 6001219 B1 | 10/2016 |

* cited by examiner

*Primary Examiner* — Sherrie Hsia
(74) *Attorney, Agent, or Firm* — Studebaker & Brackett PC

(57) ABSTRACT

A direct-viewing observation image is displayed on a monitor, and a side-viewing observation image is not displayed on the monitor. A region of interest is detected using the side-viewing observation image. A display region for observation, which displays the direct-viewing observation image, of the monitor is maintained regardless of whether or not the region of interest is detected.

16 Claims, 11 Drawing Sheets

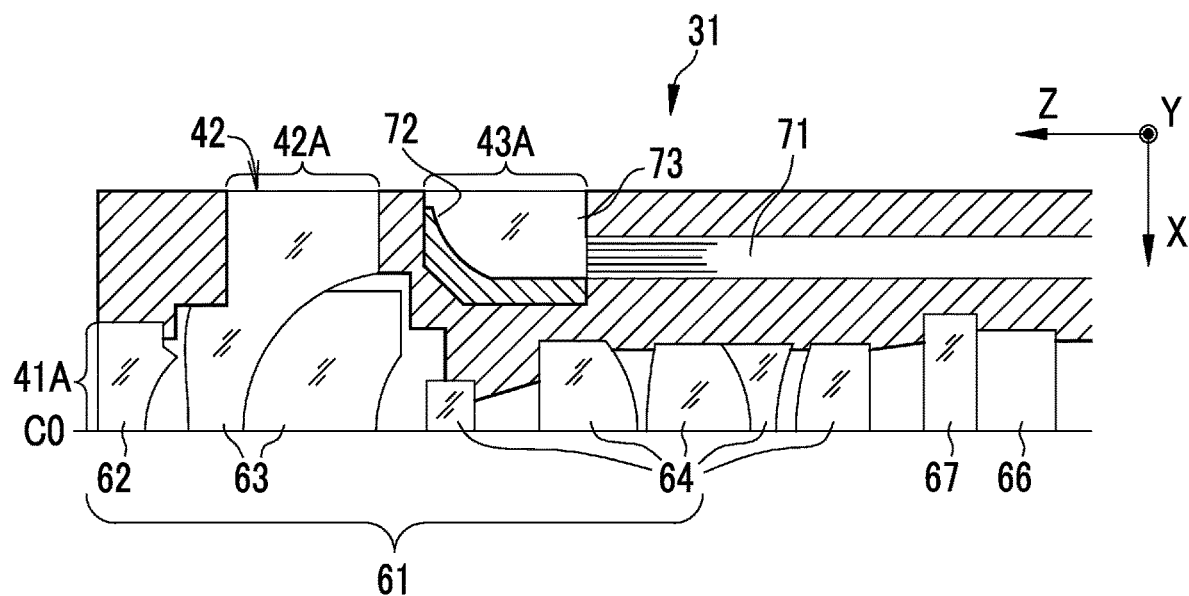

DETECTION OF REGION OF INTEREST

ENDOSCOPE SYSTEM

CROSS-REFERENCE TO RELATED APPLICATIONS

This application claims priority under 35 U.S.C § 119(a) to Japanese Patent Application No. 2018-192464 filed on Oct. 11, 2018. The above application is hereby expressly incorporated by reference, in its entirety, into the present application.

BACKGROUND OF THE INVENTION

1. Field of the Invention

The present invention relates to an endoscope system that allows direct-viewing observation and side-viewing observation to be performed.

2. Description of the Related Art

Diagnosis, which is performed using an endoscope system comprising a light source device, an endoscope, and a processor device, has become common in a medical field. In the endoscope system, the light source device generates illumination light. The endoscope includes a flexible insertion part, and the insertion part is inserted into a subject, so that an image of an object to be observed is picked up by, for example, an image sensor mounted on the distal end portion of the insertion part (hereinafter, referred to as a distal end part). Further, the processor device generates the image of the object to be observed, and displays the image of the object to be observed on a monitor.

A direct-viewing observation type endoscope that picks up an image of an object to be observed present in a direct-viewing direction representing a distal end direction of a distal end part (that is, the direction of the front along an insertion direction of an insertion part) and a side-viewing observation type endoscope that picks up an image of an object to be observed present in a side-viewing direction representing a lateral direction of a distal end part (that is, the circumferential direction of an insertion part) are known as an endoscope used in an endoscope system in the related art. Further, endoscopes that allow observation to be performed in both a direct-viewing direction and a side-viewing direction to obtain a wider angle of view as disclosed in JP5583873B (corresponding to US2015/073218A1) and JP5698879B (corresponding to US2015/265136A1) have been known in recent years.

However, in a case where observation is allowed to be performed in both the direct-viewing direction and the side-viewing direction, a direct-viewing observation image that is an image obtained in the direct-viewing direction and a side-viewing observation image that is an image obtained in the side-viewing direction are displayed on one screen. For this reason, there is a problem that it is difficult for a user to read information about the respective images. In contrast, in JP6001219B (corresponding to US2017/085762A1), only a direct-viewing observation image is basically displayed on a screen and a side-viewing observation image is displayed on the screen in a case where the amount of characteristics of a lesion is automatically detected. Accordingly, since a side-viewing observation image is displayed only in a necessary case, such as a case where a lesion is detected, to allow a user to pay attention to the direct-viewing observation image, user's concentration is maintained.

SUMMARY OF THE INVENTION

However, in JP6001219B, the size of a direct-viewing observation image is reduced to display a side-viewing observation image on the screen in a case where the side-viewing observation image is to be displayed due to the detection of a region of interest, such as a lesion part. In a case where the size of the direct-viewing observation image is changed before and after the detection of the lesion part as described above, there is a case where it is difficult for user's concentration to be maintained.

An object of the invention is to provide an endoscope system that allows user's concentration to be maintained even in a case where the detection of a region of interest is to be informed in a state where any one of a direct-viewing observation image or a side-viewing observation image is displayed on a display unit.

An endoscope system according to an aspect of the invention comprises an endoscope that includes an insertion part to be inserted into an object to be observed, a direct-viewing observation unit having a field of view in a distal end direction of the insertion part, and a side-viewing observation unit having a field of view in a lateral direction of the insertion part; an image acquisition unit that acquires a direct-viewing observation image by the direct-viewing observation unit and acquires a side-viewing observation image by the side-viewing observation unit; a display control unit that displays one of the direct-viewing observation image and the side-viewing observation image on a display unit as an image to be displayed and does not display the other thereof as an image not to be displayed; and a region-of-interest detection unit that detects a region of interest by using the image to be displayed or the image not to be displayed. The display control unit maintains a first display region, which displays the image to be displayed, of the display unit regardless of whether or not the region of interest is detected by the region-of-interest detection unit.

It is preferable that the display control unit displays a detection index, which indicates detection of the region of interest, on the display unit in a case where the region of interest is detected. It is preferable that the detection index indicates a position of the region of interest. It is preferable that the detection index is displayed in a second display region provided at a position different from a position of the first display region. It is preferable that the detection index is displayed in a third display region provided around the first display region and formed so as to correspond to a shape of the first display region. It is preferable that the third display region has an annular shape. It is preferable that a color or a shape of the detection index is changed depending on a size or the kind of the region of interest.

It is preferable that the display control unit displays a region-of-interest image, which includes a portion of the image not to be displayed where the region of interest is detected, on the display unit in a case where the region of interest is detected. It is preferable that the display control unit cancels the non-display of a portion where the region of interest is detected and displays the portion on the display unit in a case where the region of interest is detected. It is preferable that the display control unit electronically magnifies the image to be displayed and displays the image to be displayed on the display unit. It is preferable that the image acquisition unit acquires the direct-viewing observation image and the side-viewing observation image from an image obtained from one image sensor. It is preferable that the direct-viewing observation image is acquired from an image sensor for acquiring a direct-viewing observation image and the side-viewing observation image is acquired from an image sensor for acquiring a side-viewing observation image different from the image sensor for acquiring a direct-viewing observation image. It is preferable that the endoscope system further comprises a mode changeover switch switching a normal display mode where both the direct-viewing observation image and the side-viewing observation image are displayed on the display unit and a specific display mode where the image to be displayed is displayed on the display unit and the image not to be displayed is not displayed.

It is preferable that the endoscope system further comprises a brightness information acquisition unit acquiring brightness information for an image not to be displayed from the image not to be displayed and gain processing for obtaining target brightness is performed on the image not to be displayed on the basis of the brightness information for an image not to be displayed. It is preferable that the endoscope system further comprises an image processing unit performing image processing, which is different for each frame, on the image not to be displayed. It is preferable that the direct-viewing observation unit is provided with a direct-viewing observation window and the side-viewing observation unit is provided with a side-viewing observation window, a fluid feed line for side-viewing for feeding cleaning fluid to a nozzle for side-viewing to be used for cleaning the side-viewing observation window is provided separately from a fluid feed line for direct-viewing for feeding the cleaning fluid to a nozzle for direct-viewing to be used for cleaning the direct-viewing observation window, and the cleaning fluid is automatically ejected to the side-viewing observation window through the fluid feed line for side-viewing and the nozzle for side-viewing in a case where a foreign matter is detected in the image not to be displayed.

According to the invention, it is possible to maintain user's concentration even in a case where the detection of a region of interest is to be informed in a state where any one of a direct-viewing observation image or a side-viewing observation image is displayed on a display unit.

BRIEF DESCRIPTION OF THE DRAWINGS

FIG. 4 is a cross-sectional view of a part of a first protruding portion.

FIG. 5 is a cross-sectional view of a second protruding portion.

FIG. 17 is a block diagram showing an endoscope system that comprises a pump for direct-viewing, a pump for side-viewing, and the like.

DESCRIPTION OF THE PREFERRED EMBODIMENTS

Figure 1:
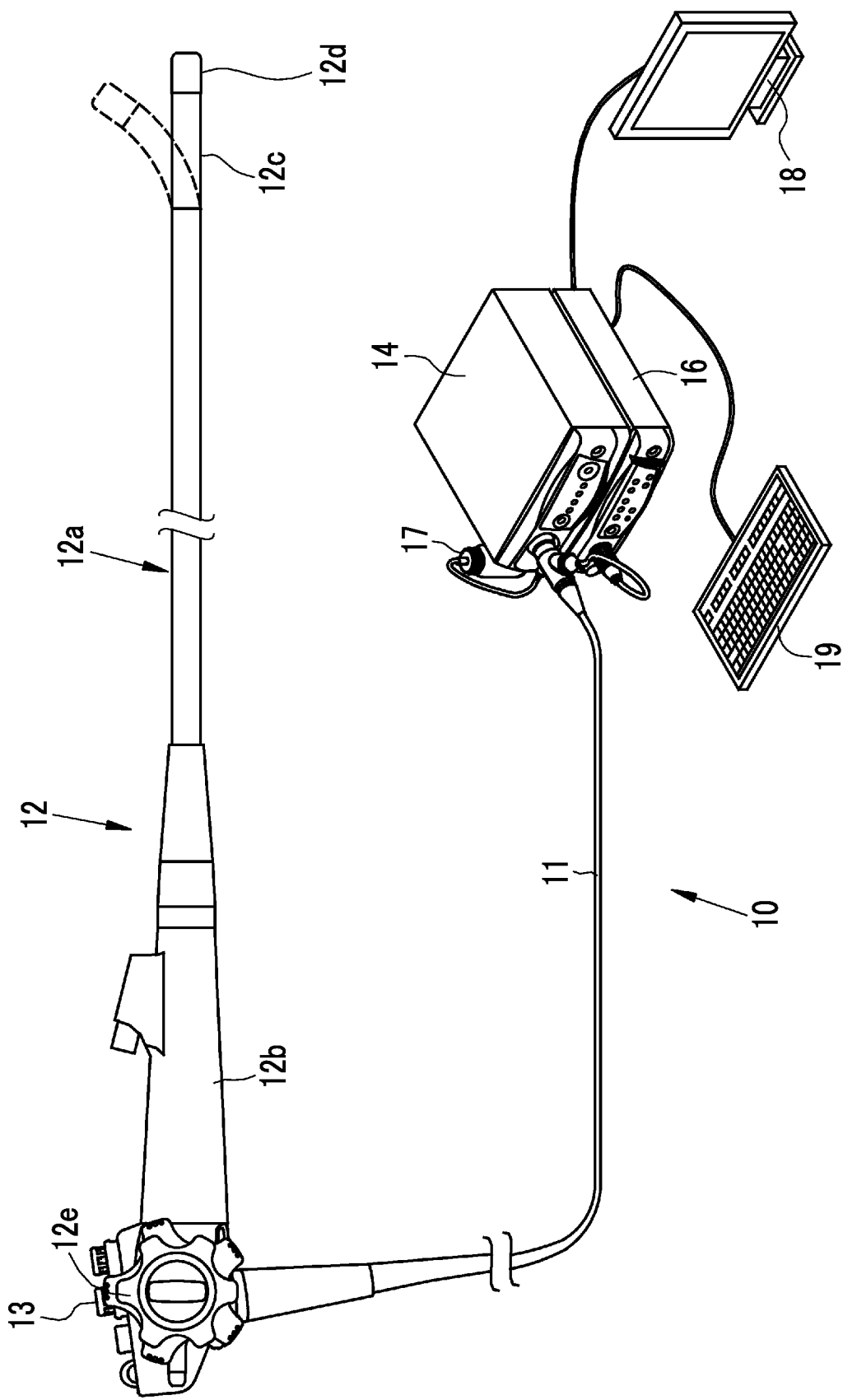
FIG. 1 is a diagram showing the appearance of an endoscope system.

As shown in FIG. 1, an endoscope system 10 includes an endoscope 12 that picks up the image of an object to be observed, a light source device 14 that generates illumination light, a processor device 16 that generates an image for observation (hereinafter, referred to as an observation image) by using an image obtained from the image pick-up of the object to be observed (hereinafter, referred to as a picked-up image), a monitor 18 that is a display unit displaying the observation image, and a user interface 19 that is one of user interfaces. The endoscope 12 is optically connected to the light source device 14 by a universal cord 11 and is electrically connected to the processor device 16. Further, the endoscope 12 is connected to a tank 17, which stores cleaning fluid (for example, water) or the like, by the universal cord 11. A mechanism, such as a pump, for sending the cleaning fluid or the like of the tank 17 is provided in, for example, the light source device 14. A keyboard is provided in FIG. 1 as the user interface 19, but others, such as a mouse and a touch pad may be provided.

The endoscope 12 includes an insertion part 12a that is to be inserted into a subject, an operation part 12b that is provided at the proximal end portion of the insertion part 12a, a bendable part 12c that is provided on the distal end side of the insertion part 12a, and a distal end part 12d. In a case where an angle knob 12e provided on the operation part 12b is operated, the bendable part 12c is bent. As a result of the bend of the bendable part 12c, the distal end part 12d faces in a desired direction.

Further, the operation part 12b includes, for example, a cleaning switch 13a, which is used to eject cleaning fluid from nozzles provided in the distal end part 12d, in addition to the angle knob 12e. In a case where the cleaning switch 13a is pressed in a state where dirt adheres to the distal end part 12d due to contact between the object to be observed and the distal end part 12d or the like, the cleaning fluid is ejected toward at least a part of the distal end part 12d from the nozzles provided in the distal end part 12d. As a result, a portion of the distal end part 12d to which the cleaning fluid is ejected can be cleaned. In the endoscope system 10, the cleaning fluid is liquid, such as water or liquid medicine. Further, for convenience' sake, cleaning "fluid" is described in this specification. However, as long as being used for cleaning, gas, such as air, solid, a mixture of materials having different phases, and the like, which are to be ejected from the nozzles, are also included in the "cleaning fluid".

Furthermore, the operation part 12b is provided with a mode changeover switch 13b. In this embodiment, as described later, the endoscope system 10 has two modes, that is, a normal display mode (see FIG. 8) where a direct-viewing observation image 100 obtained using a direct-viewing observation unit 41 is displayed at the central portion of a monitor 18 and a side-viewing observation image 102 obtained using a side-viewing observation unit 42 is displayed at the outer peripheral portion of the direct-viewing observation image 100, and a specific display mode where the direct-viewing observation image 100 is enlarged and displayed on the monitor 18 and the side-viewing observation image is used for only the detection of a region of interest and is not displayed on the monitor 18. The normal display mode and the specific display mode are switched by the mode changeover switch 13b.

Figure 2:
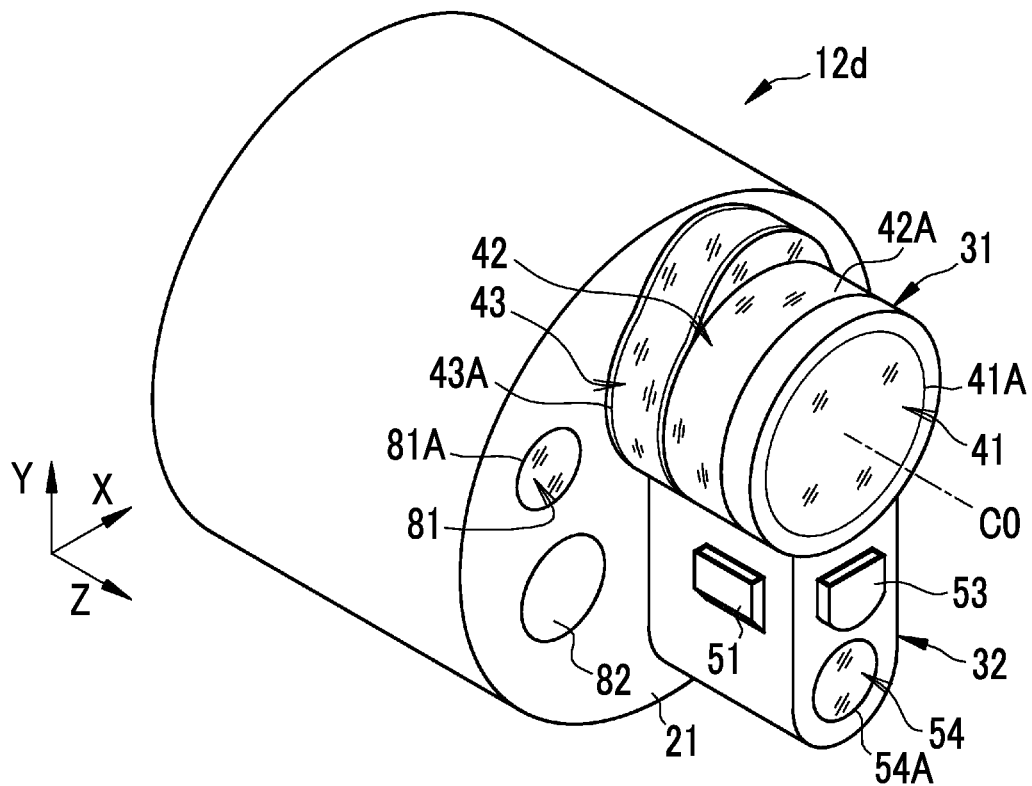
FIG. 2 is a perspective view showing the appearance of a distal end part.
Figure 3:
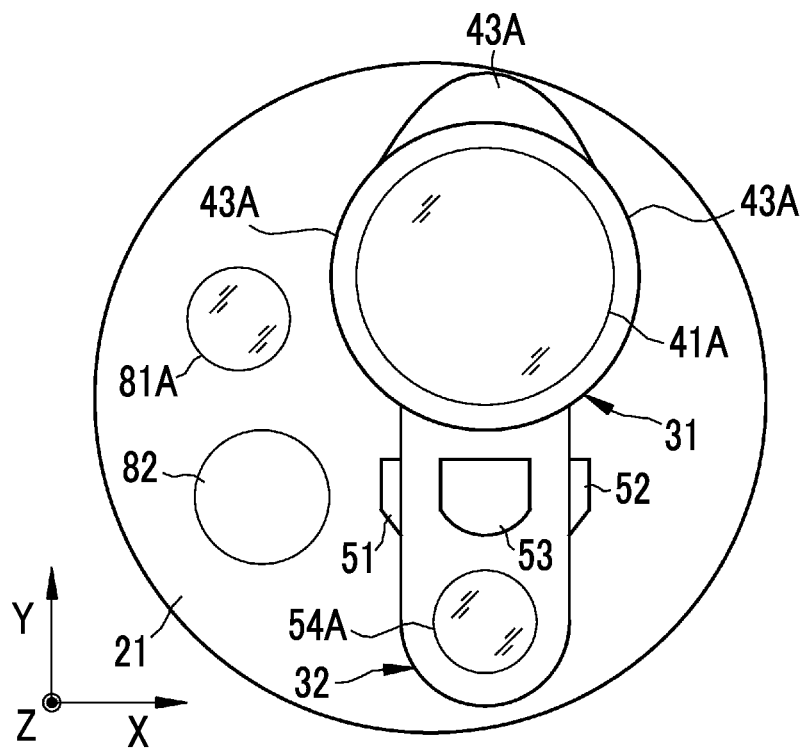
FIG. 3 is a front view of the distal end part.

As shown in FIGS. 2 and 3, the distal end part 12d of the insertion part 12a to be inserted into an object to be observed includes two protruding portions, that is, first and second protruding portions 31 and 32 further protruding from a distal end face 21 of the distal end part 12d in a Z direction that is a distal end direction of the insertion part 12a. The first protruding portion 31 and the second protruding portion 32 are adjacent to each other. Hereinafter, a direction toward the first protruding portion 31 from the second protruding portion 32 is referred to as a Y direction, and a direction perpendicular to the Z direction and the Y direction is referred to as an X direction. Since the Z direction is the field-of-view direction of the direct-viewing observation unit 41, the Z direction is also referred to as a direct-viewing direction. Further, since the Y direction is the field-of-view direction of the side-viewing observation unit 42, the Y direction is also referred to as a side-viewing direction. Furthermore, the positive side of the insertion part 12a, the distal end part 12d, the first protruding portion 31, or the second protruding portion 32 in the X direction is referred to as "left", and the negative side thereof in the X direction is referred to as "right". The positive side of the insertion part 12a, the distal end part 12d, the first protruding portion 31, or the second protruding portion 32 in the Z direction is referred to as "front" or a "distal end (distal end side)", and the negative side thereof in the Z direction is referred to as a "proximal end (proximal end side)".

The first protruding portion 31 has a substantially cylindrical shape as a whole; and comprises a direct-viewing observation window 41A that is provided at the distal end thereof and is an observation window for the direct-viewing observation unit 41 and a side-viewing observation window 42A that is provided on the side surface thereof and is an observation window for the side-viewing observation unit 42. The direct-viewing observation unit 41 has a field of view in the distal end direction of the insertion part 12a, and picks up an image of an object to be observed that is present in the distal end direction of the insertion part 12a. The direct-viewing observation unit 41 includes, for example, an image pickup lens, an image sensor, and the like. An optical member, such as the image pickup lens of the direct-viewing observation unit 41, or a transparent protective member that protects the optical member, such as the image pickup lens, is exposed to the distal end (the surface facing in the Z direction) of the first protruding portion 31. A portion, which is exposed to the distal end of the first protruding portion 31, is the direct-viewing observation window 41A that takes in light incident from the object to be observed present in the distal end direction of the insertion part 12a.

The side-viewing observation unit 42 has a field of view in the lateral direction of the insertion part 12a, and picks up an image of an object to be observed that is present in the lateral direction of the insertion part 12a. The side-viewing observation unit 42 includes, for example, an image pickup lens, an image sensor, and the like as with the direct-viewing observation unit 41. However, an optical member, such as the image pickup lens of the side-viewing observation unit 42, or a transparent protective member that protects the optical member, such as the image pickup lens, is exposed to the side surface of the first protruding portion 31 (the surface forming the outer periphery of the first protruding portion 31). A portion, which is exposed to the side surface of the first protruding portion 31, is the side-viewing observation window 42A that takes in light incident from the object to be observed present in the lateral direction of the insertion part 12a. In the endoscope 12 of this embodiment, the side-viewing observation unit 42 is exposed to the outside over the circumference in the circumferential direction of the first protruding portion 31 except for a joint portion between the first protruding portion 31 and the second protruding portion 32, and forms one belt-like side-viewing observation window 42A.

Further, the first protruding portion 31 includes a direct-viewing/side-viewing illumination window 43A, which is an illumination window for a direct-viewing/side-viewing illumination unit 43, in addition to the direct-viewing observation window 41A and the side-viewing observation window 42A. The direct-viewing/side-viewing illumination unit 43 emits illumination light toward the fields of view of the direct-viewing observation unit 41 and the side-viewing observation unit 42 from the direct-viewing/side-viewing illumination window 43A. The direct-viewing/side-viewing illumination unit 43 includes, for example, a light guide that guides the illumination light emitted from the light source device 14, and optical members, such as lenses or mirrors, that diffuse and emit the illumination light guided to the distal end part 12d by the light guide toward the fields of view of the direct-viewing observation unit 41 and the side-viewing observation unit 42. The optical members, such as mirrors, of the direct-viewing/side-viewing illumination unit 43 or transparent protective members protecting the optical members, such as mirrors, are exposed to the side surface of the first protruding portion 31. A portion, which is exposed to the side surface of the first protruding portion 31, is the direct-viewing/side-viewing illumination window 43A that emits illumination light in the lateral direction of the insertion part 12a. In the endoscope 12 of this embodiment, a part of the outer periphery of the first protruding portion 31 except for the joint portion between the first protruding portion 31 and the second protruding portion 32 forms the direct-viewing/side-viewing illumination window.

In this embodiment, the direct-viewing observation unit 41 and the side-viewing observation unit 42 include a common image pickup lens 61 and a common image sensor 66 as shown in FIG. 4. The image pickup lens 61 consists of a front group lens 62, a mirror lens 63 that is formed of two lenses joined to each other, and a rear group lens 64. The front surface of the front group lens 62 is exposed to the distal end of the first protruding portion 31. That is, the front surface of the front group lens 62 forms the direct-viewing observation window 41A of the direct-viewing observation unit 41. Further, the side surface of the mirror lens 63 is exposed to the side surface of the first protruding portion 31. For this reason, the side surface of the mirror lens 63 forms the side-viewing observation window 42A of the side-viewing observation unit 42.

The mirror lens 63 guides light, which is incident through the front group lens 62 from an object to be observed present in the distal end direction of the insertion part 12*a*, to the rear group lens 64. Then, the light forms an image on the image pickup surface of the image sensor 66 through a cover glass 67. Accordingly, the image pickup lens 61 and the image sensor 66 serving as the direct-viewing observation unit 41 pick up an image of the object to be observed that is present in the distal end direction of the insertion part 12*a*.

On the other hand, the mirror lens 63 sequentially reflects light, which is incident through the side surface of the mirror lens 63 from an object to be observed present in the lateral direction of the insertion part 12*a*, by a joint surface between the two lenses of the mirror lens 63 and the front surface of the mirror lens 63, and guides the light to the rear group lens 64. Then, the light forms an image on the image pickup surface of the image sensor 66 through the cover glass 67. Accordingly, the image pickup lens 61 and the image sensor 66 serving as the side-viewing observation unit 42 pick up an image of the object to be observed that is present in the lateral direction of the insertion part 12*a*.

Further, the direct-viewing/side-viewing illumination unit 43 includes a light guide 71, a reflective member 72, and a filling member 73. The light guide 71 is optically connected to the light source device 14, and guides illumination light that is emitted from the light source device 14. Then, the illumination light is emitted to the reflective member 72 from the end face of the light guide 71 through the filling member 73. The reflective member 72 diffuses the illumination light, which is incident from the light guide 71, in the lateral direction of the insertion part 12*a*, and emits the illumination light to a range that includes the field of view of at least the side-viewing observation unit 42. The filling member 73 is a protective member that protects the emission end face of the light guide 71 and the reflective member 72, and is transparent. Furthermore, the filling member 73 smoothly fills a groove portion, which is formed between the light guide 71 and the reflective member 72, along the side surface of the first protruding portion 31. For this reason, the filling member 73 forms the direct-viewing/side-viewing illumination window 43A.

In the endoscope 12 of this embodiment, the side-viewing observation window 42A is provided on the side surface of the first protruding portion 31 so as to be close to the distal end of the first protruding portion 31, and the direct-viewing/side-viewing illumination window 43A is provided on the side surface of the first protruding portion 31 so as to be close to the proximal end of the first protruding portion 31. However, the positions and the order of the side-viewing observation window 42A and the direct-viewing/side-viewing illumination window 43A are random. However, in a case where the side-viewing observation window 42A is provided on the side surface of the first protruding portion 31 so as to be close to the distal end of the first protruding portion 31, vignetting or the like caused by the distal end face 21 or the like is prevented and the field of view of the direct-viewing/side-viewing illumination unit 43 is easily ensured. Accordingly, it is good that the side-viewing observation window 42A is provided on the side surface of the first protruding portion 31 so as to be close to the distal end of the first protruding portion 31 as much as possible.

As shown in FIGS. 2 and 3, the second protruding portion 32 includes nozzles that eject cleaning fluid to clean the distal end part 12*d*. More specifically, the second protruding portion 32 includes a nozzle 51 and a nozzle 52 that eject cleaning fluid toward the side-viewing observation window 42A. The nozzle 51 is provided on the right side surface of the second protruding portion 32, and the nozzle 52 is provided on the left side surface of the second protruding portion 32. The nozzles 51 and 52 have the same properties in terms of being provided on the second protruding portion 32 and cleaning the side-viewing observation window 42A by ejecting cleaning fluid toward the side-viewing observation window 42A. The second protruding portion 32 further includes a nozzle 53 provided at the distal end of the second protruding portion 32. The nozzle 53 cleans the direct-viewing observation window 41A by ejecting cleaning fluid toward the direct-viewing observation window 41A that is an exposed portion of the direct-viewing observation unit 41. In this embodiment, an operation related to the cleaning of the direct-viewing observation window 41A or the side-viewing observation window 42A to be performed in the normal display mode is different from an operation related to the cleaning of the direct-viewing observation window 41A or the side-viewing observation window 42A to be performed in the specific display mode. The details of the operations related to the cleaning to be performed in these two modes will be described later.

As shown in FIGS. 3 and 5, the second protruding portion 32 includes a direct-viewing illumination window 54A that is an illumination window for a direct-viewing illumination unit 54 emitting illumination light toward the field of view of the direct-viewing observation unit 41. The direct-viewing illumination unit 54 includes, for example, a light guide 77 that guides the illumination light emitted from the light source device 14, an illumination lens 78 that diffuses and emits the illumination light guided to the distal end part 12*d* by the light guide 77 toward the field of view of the direct-viewing observation unit 41, and the like. The illumination lens of the direct-viewing illumination unit 54 or a transparent protective member, which protects the illumination lens, is exposed to the distal end of the second protruding portion 32. A portion, which is exposed to the distal end of the second protruding portion 32, is the direct-viewing illumination window 54A. In this embodiment, the front surface of the illumination lens 78 is exposed to the distal end of the second protruding portion 32. For this reason, the front surface of the illumination lens 78 forms the direct-viewing illumination window 54A.

As shown in FIGS. 2 and 3, the distal end face 21 of the distal end part 12*d* includes a direct-viewing illumination window 81A, which is an illumination window for a direct-viewing illumination unit 81, and a forceps port 82 at positions on the right side of the first protruding portion 31 and the second protruding portion 32. The direct-viewing illumination unit 81 emits illumination light toward the field of view of the direct-viewing observation unit 41 as with the direct-viewing illumination unit 54 that is provided at the second protruding portion 32. An illumination lens of the direct-viewing illumination unit 81 or a transparent protective member protecting the illumination lens is exposed to the distal end face 21. A portion exposed to the distal end face 21 is the direct-viewing illumination window 81A.

The forceps port 82 is an outlet for a treatment tool, such as forceps. In a case where a treatment tool, such as forceps, is inserted from an inlet (not shown) that is provided at the proximal end portion of the endoscope 12, the treatment tool reaches the forceps port 82 through a forceps channel and the distal end of the treatment tool can protrude from the forceps port 82. The forceps channel communicates with the distal end part 12*d*, the insertion part 12*a*, and the operation part 12*b*.

Figure 6:
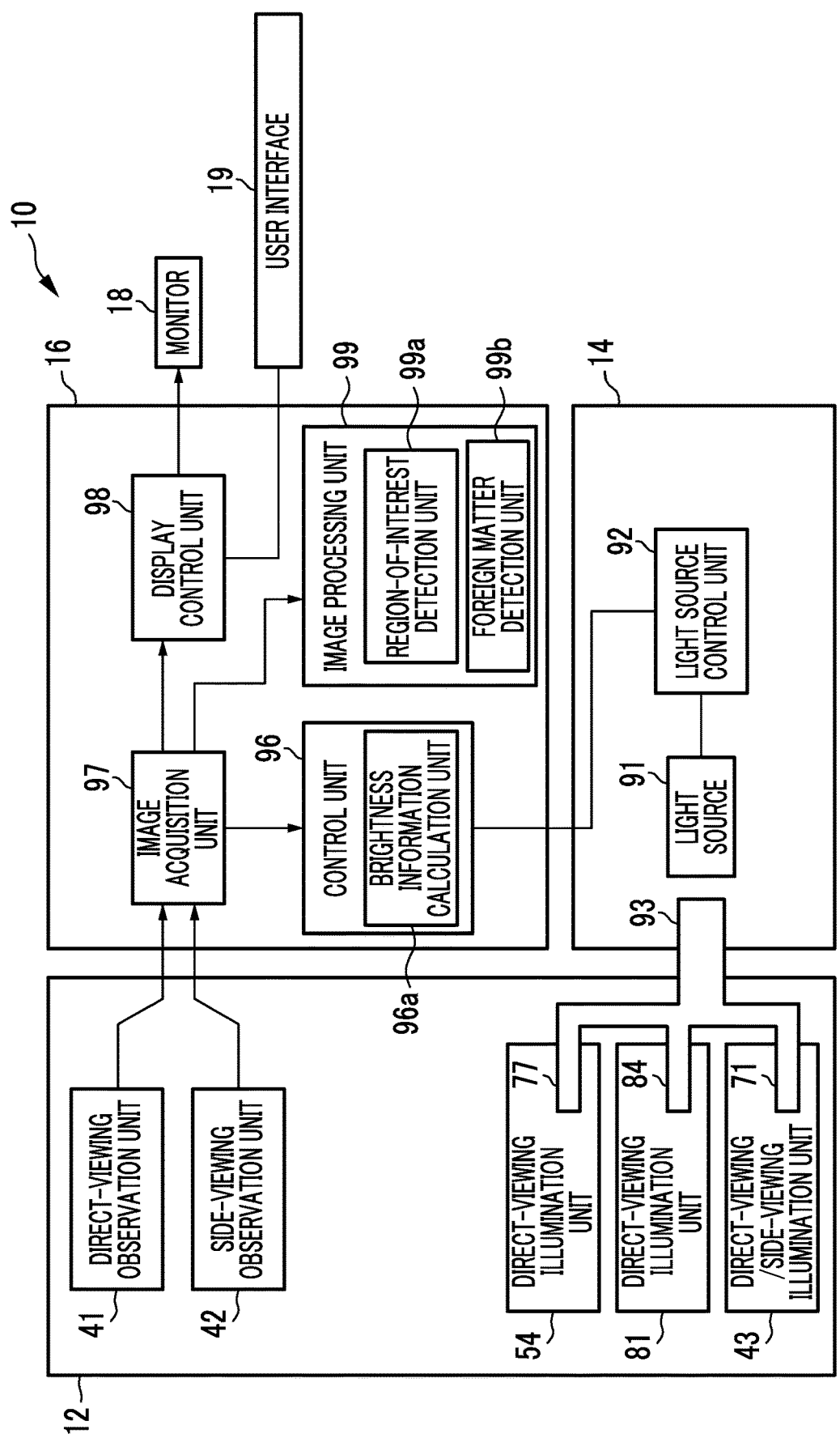
FIG. 6 is a block diagram of the endoscope system.

As shown in FIG. 6, the light source device 14 comprises a light source 91 that generates illumination light, and a light source control unit 92 that controls the light source 91. The light source 91 includes, for example, a plurality of light emitting diodes (LEDs) that can be independently controlled and emit light having different wavelengths or different wavelength ranges. Other semiconductor light sources, such as laser diodes (LD), may be used as the light source 91 instead of LEDs. A combination of a semiconductor light source, a fluorescent substance, which uses light emitted from the semiconductor light source as excitation light to emit light having other colors, and the like may be used as the light source. A lamp light source, such as a xenon lamp, may also be used as the light source 91. Further, the light source 91 may be formed of a semiconductor light source, a combination of a semiconductor light source and a fluorescent substance, or a combination of a lamp light source and an optical filter that adjusts a wavelength band or a spectrum. Plural kinds of illumination light can be emitted in a case where a combination of, for example, a white LED and an optical filter is used.

The light source control unit 92 controls each of the turn-on, the turn-off, and the amount of light of the LEDs or the like of the light source 91 according to the drive timing of the image sensor 66. Particularly, in a case where one observation image is generated using a plurality of picked-up images (that is, a multi-frame observation mode), the light source control unit 92 can change the wavelength band or the spectrum of the illumination light for every image pickup frame where a plurality of picked-up images to be used for the generation of an observation image are obtained, as the result of the control of the LEDs or the like.

Illumination light, which is emitted from the light source 91, is incident on a light guide 93. Since the light guide 93 is inserted into the endoscope 12 and the universal cord from the light source device 14, the light guide 93 transmits the illumination light up to the distal end part 12*d* of the endoscope 12. The light guide 93 is branched to at least the light guide 77 of the direct-viewing illumination unit 54, a light guide 84 of the direct-viewing illumination unit 81, and the light guide 71 of the side-viewing illumination unit 43, and transmits the illumination light to each of these illumination units. A multimode fiber can be used as the light guide 93 and each branched light guide, such as the light guide 71. For example, a thin fiber cable of which a total diameter of a core diameter of 105 μm, a cladding diameter of 125 μm, and a protective layer forming a covering is in the range of φ 0.3 to 0.5 mm can be used.

The processor device 16 comprises a control unit 96, an image acquisition unit 97, a display control unit 98, and an image processing unit 99. The control unit 96 is a central processing unit (CPU) that generally controls the endoscope system 10. The control unit 96 performs, for example, synchronization control for causing the image pickup timing of the image sensor 66 to coincide with the light-emitting timing of each LED or the like of the light source 91. The control of the light-emitting timing of each LED or the like of the light source 91 is performed through the light source control unit 92. In this embodiment, the control unit 96 drives the image sensor 66 at a fixed timing. Further, the control unit 96 performs auto exposure control (AE control) for automatically controlling exposure. AE control to be performed in the normal display mode is different from AE control to be performed in the specific display mode. The details of AE control to be performed in the normal display mode and the specific display mode will be described later.

Figure 7:
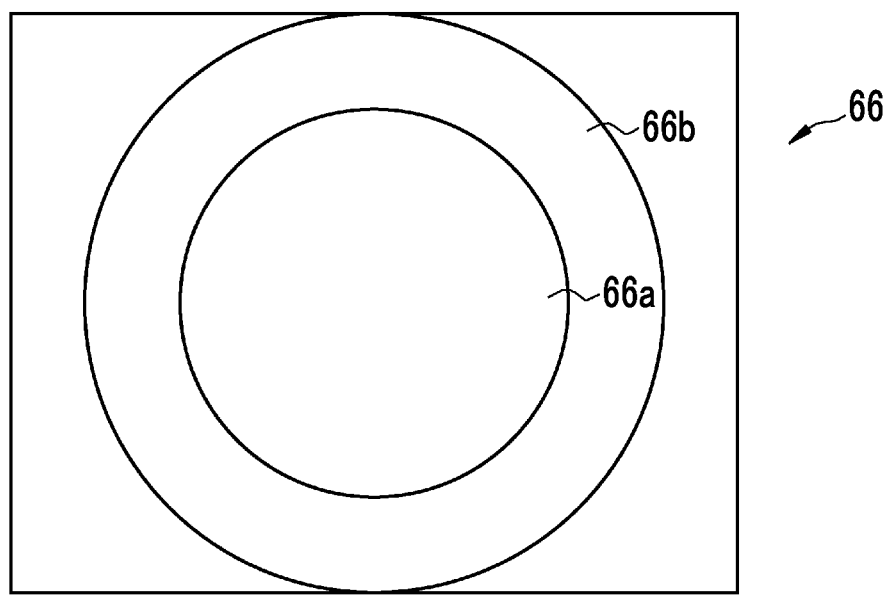
FIG. 7 is a diagram showing an image sensor.

The image acquisition unit 97 acquires a direct-viewing observation image by the direct-viewing observation unit 41, and acquires a side-viewing observation image by the side-viewing observation unit 42. In this embodiment, the direct-viewing observation unit 41 and the side-viewing observation unit 42 share the image pickup lens 61 and the image sensor 66. The image acquisition unit 97 acquires an image picked by by the image sensor 66. Specific processing is performed on the image acquired by the image acquisition unit 97, so that a picked-up image including the direct-viewing observation image and a side-viewing observation image is obtained. As shown in FIG. 7, an image obtained by a circular direct-viewing image pickup region 66*a*, which is provided at the central portion of the image sensor 66, is referred to as a direct-viewing observation image and an image obtained by a side-viewing image pickup region 66*b*, which is provided outside the direct-viewing image pickup region of the image sensor 66, is referred to as a side-viewing observation image. The direct-viewing observation image and the side-viewing observation image, which are obtained by the image acquisition unit 97, are sent to the display control unit 98 or the image processing unit 99.

Figure 8:
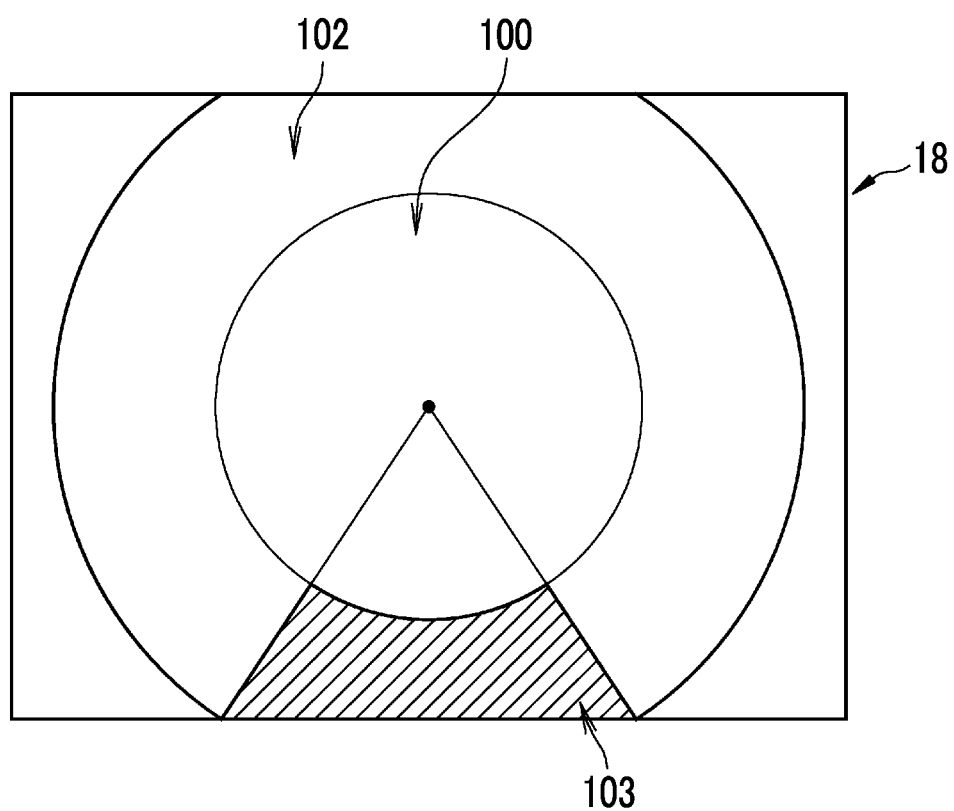
FIG. 8 is an image diagram of a monitor that displays a direct-viewing observation image and a side-viewing observation image.

The display control unit 98 acquires the direct-viewing observation image and the side-viewing observation image from the image acquisition unit 97. Then, the display control unit 98 displays the direct-viewing observation image or the side-viewing observation image on the monitor 18. In a case where the endoscope system 10 is set to the normal display mode, the display control unit 98 displays both the direct-viewing observation image 100 and the side-viewing observation image 102 on the monitor 18 as shown in FIG. 8. The side-viewing observation image 102 includes a blind spot portion 103 where an image of an object to be observed cannot be picked up since the object to be observed is not present in the field of view of the side-viewing observation unit 42.

Figure 9:
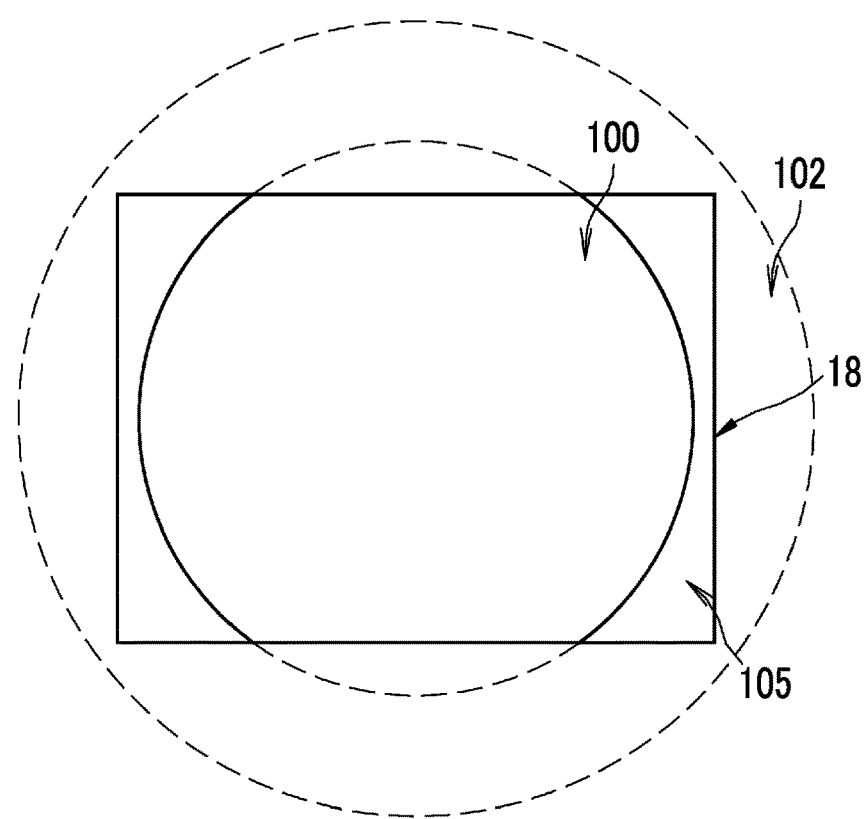
FIG. 9 is an image diagram of the monitor that displays only a direct-viewing observation image.

On the other hand, in a case where the endoscope system 10 is set to the specific display mode, the display control unit 98 displays only the direct-viewing observation image 100 (an image to be displayed) on the monitor 18 and does not display (undisplays) the side-viewing observation image 102 (an image not to be displayed) on the monitor 18 as shown in FIG. 9. The side-viewing observation image 102 is used to detect a region of interest, which is included in an object to be observed, by a region-of-interest detection unit 99*a* (see FIG. 6). The display control unit 98 controls the display of the monitor 18 according to the result of detection of the region of interest. The detail of the control of display based on the result of detection of a region of interest will be described later. In the specific display mode, the direct-viewing observation image 100 is electronically magnified to be displayed on the entire screen of the monitor 18. Further, an image 105, which is to be displayed on the screen of the monitor 18, of the side-viewing observation image 102 is not displayed on the monitor 18 by mask processing or the like. In the specific display mode, the side-viewing observation image may be used as an image not to be displayed and the direct-viewing observation image may be used as the image to be displayed.

The image processing unit 99 performs various kinds of image processing, which correspond to the normal display mode or the specific display mode, on the direct-viewing observation image or the side-viewing observation image. The various kinds of image processing include gain processing, color emphasis processing, structure emphasis processing, and the like. Since both the direct-viewing observation image and the side-viewing observation image are displayed on the monitor 18 in a case where the endoscope system 10 is set to the normal display mode, it is preferable that the same image processing is performed on each of the direct-viewing observation image and the side-viewing observation image. On the other hand, since only the direct-viewing observation image is displayed on the monitor 18 and the direct-viewing observation image is not displayed on the monitor 18 in a case where the endoscope system 10 is set to the specific display mode, image processing to be performed on the direct-viewing observation image may be different from image processing to be performed on the side-viewing observation image.

For example, since the direct-viewing observation image is to be displayed on the monitor 18, it is preferable that image processing for allowing a user to easily and visually recognize the direct-viewing observation image is performed on the direct-viewing observation image as the image processing to be performed on the direct-viewing observation image. On the other hand, since the side-viewing observation image is used to detect a region of interest, it is preferable that image processing for allowing a region of interest to be easily detected is performed as the image processing to be performed on the side-viewing observation image. For example, it is preferable that high frequency emphasis processing is performed as structure emphasis processing in a case where a region of interest is a tiny superficial blood vessel or the like. Further, it is preferable that redness emphasis processing for emphasizing redness is performed in a case where a region of interest is redness or the like. Furthermore, image processing different for each frame may be performed on the side-viewing observation image so that a plurality of regions of interest are easily detected. Since the side-viewing observation image is not displayed on the monitor 18, the side-viewing observation image does not stress a user out even though image processing is changed for each frame.

For example, in a case where side-viewing observation images are acquired at a plurality of frames including a first frame and a second frame, high frequency emphasis processing may be performed on a side-viewing observation image acquired at the first frame and redness emphasis processing may be performed on a side-viewing observation image acquired at the second frame. In this case, a superficial blood vessel is easily detected from the side-viewing observation image, which is acquired at the first frame, as a region of interest and redness is easily detected from the side-viewing observation image, which is acquired at the second frame, as a region of interest.

Further, the image processing unit 99 includes a region-of-interest detection unit 99a that performs region-of-interest detection processing for detecting a region of interest from the side-viewing observation image in a case where the endoscope system 10 is set to the specific display mode, and a foreign matter detection unit 99b that detects whether or not a foreign matter adheres to the side-viewing observation window 42A from the side-viewing observation image in a case where the endoscope system 10 is set to the specific display mode. In a case where the foreign matter detection unit 99b detects a foreign matter, processing for ejecting cleaning fluid to the side-viewing observation window 42A is automatically performed. The detail of automatic cleaning based on the detection of a foreign matter will be described in detail later. Even if a region of interest is overlooked in the direct-viewing direction, the overlooked region of interest passes through a region in the side-viewing direction in most cases. Accordingly, it is preferable that the region-of-interest detection unit 99a detects a region of interest from the side-viewing observation image. In a case where a range for the detection of a region of interest is limited, a load on the amount of calculation for detection can be reduced. However, the region-of-interest detection unit 99a may be adapted to detect a region of interest from the direct-viewing observation image.

For example, Neural Network (NN), Convolutional Neural Network (CNN), Adaboost, Random Forest, and the like may be used as the region-of-interest detection processing. Further, as the region-of-interest detection processing, the detection of a region of interest may be performed on the basis of the amount of characteristics that is obtained from the color information, the gradient of pixel values, and the like of the side-viewing observation image. The gradient of pixel values, and the like are changed depending on, for example, the shape (the overall undulation, the local recess or protuberance, or the like of a mucous membrane), the color (a color, such as whitening caused by inflammation, bleeding, redness, or atrophy), the characteristics of a tissue (the thickness, the depth, or the density of a blood vessel, a combination thereof, or the like), the characteristics of structure (a pit pattern, and the like), or the like of a subject.

A region of interest, which is to be detected by the region-of-interest detection unit 99a, is a region including, for example, a lesion part typified by a cancer, a benign tumor, an inflamed part (including a part where a change, such as bleeding or atrophy, occurs in addition to so-called inflammation), a colonic diverticulum, an treatment scar (an endoscopic mucosal resection (EMR) scar, an endoscopic submucosal dissection (ESD) scar, and a clipped portion), a blood point, a perforation, a marking portion marked by blood vessel heteromorphism, a cautery mark caused by heating, or coloring using a colorant, a fluorescent agent, or the like, or a biopsy portion where biopsy is performed. That is, a region including a lesion; a region where a lesion is likely to occur; a region that has been subjected to a certain treatment, such as biopsy; a treatment tool, such as a clip or forceps; a region where detailed observation is needed regardless of the possibility of a lesion, such as a dark region (a region where observation light does not easily reach since the region is positioned on the back of a fold or in a lumen); or the like may be the region of interest. In the endoscope system 10, the region-of-interest detection unit 99a detects a region, which includes at least one of a lesion part, a benign tumor, an inflamed part, a colonic diverticulum, a treatment scar, a blood point, a perforation, a marking portion marked by blood vessel heteromorphism, or a biopsy portion, as the region of interest.

Figure 10:
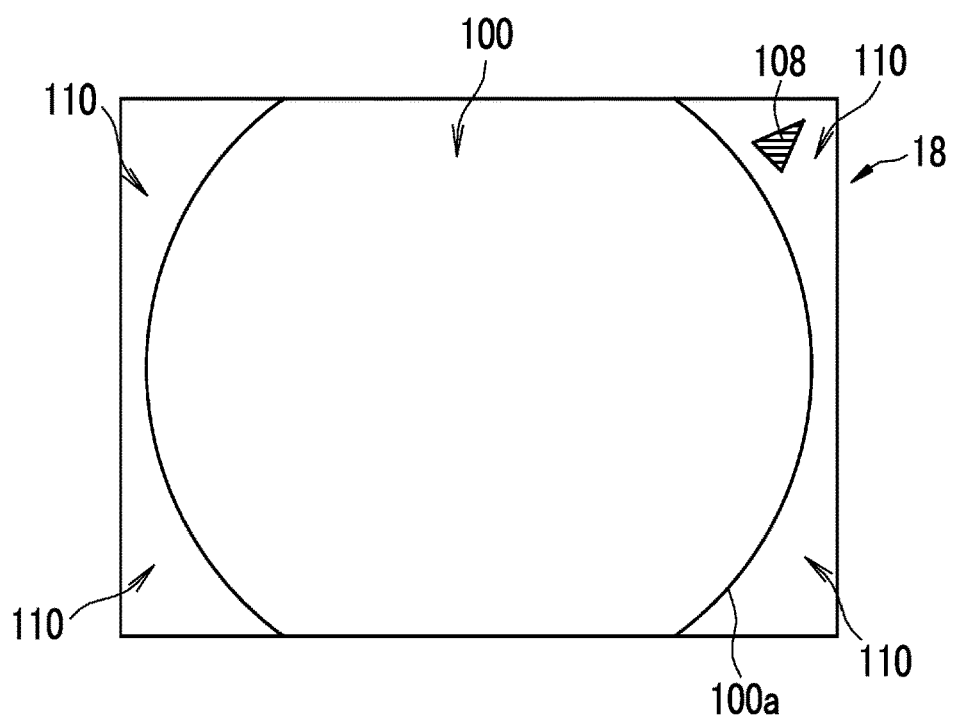
FIG. 10 is an image diagram of the monitor that displays a direct-viewing observation image and a detection index.

The control of display based on the result of detection of a region of interest will be described below. In a case where a region of interest is detected, as shown in FIG. 10, the display control unit 98 informs a user of the detection of the region of interest with the monitor 18 in a state where a display region 100a for observation (first display region) for displaying the direct-viewing observation image 100 is maintained. Accordingly, since the display aspect of the direct-viewing observation image 100 at which the user gazes is maintained even in a case where the region of interest is detected, user's attention can be maintained. The maintaining of the display region for observation means that the size or shape of the display region for the region of interest is maintained. Further, it is preferable that a ratio of a width to a height (screen aspect ratio) of the screen of the monitor 18 shown in FIG. 10 is 4:3.

Furthermore, in regard to the informing of the detection of a region of interest, the detection index 108 indicating the detection of the region of interest or the position of the region of interest is displayed in a peripheral region 110 (second display region), which is provided at a position separate from the display region 100*a* for observation displaying the direct-viewing observation image, of the monitor 18. An arrow of the detection index 108 is displayed at the upper left portion of the side-viewing observation image to show the detection of the region of interest. Since the detection index 108 is displayed in this way, the user operates the angle knob 12*e* to move the distal end part 12*d* of the endoscope so that the region of interest enters the field of view of the direct-viewing observation unit 41. Since the region of interest enters the field of view of the direct-viewing observation unit 41, the user can grasp the contents of the region of interest. Since the peripheral region 110 is provided at four corners of the screen of the monitor 18, the detection index 108 is displayed at any one of the four corners. The arrow having a fixed size and a specific color is used in FIG. 10 as the detection index, but the color or the shape of the detection index may be changed depending on the size or the kind of the region of interest. For example, the detection index may have a blue color in a case where the region of interest is a treatment tool, and the detection index may have a red color in a case where the region of interest is a lesion.

Figure 11:
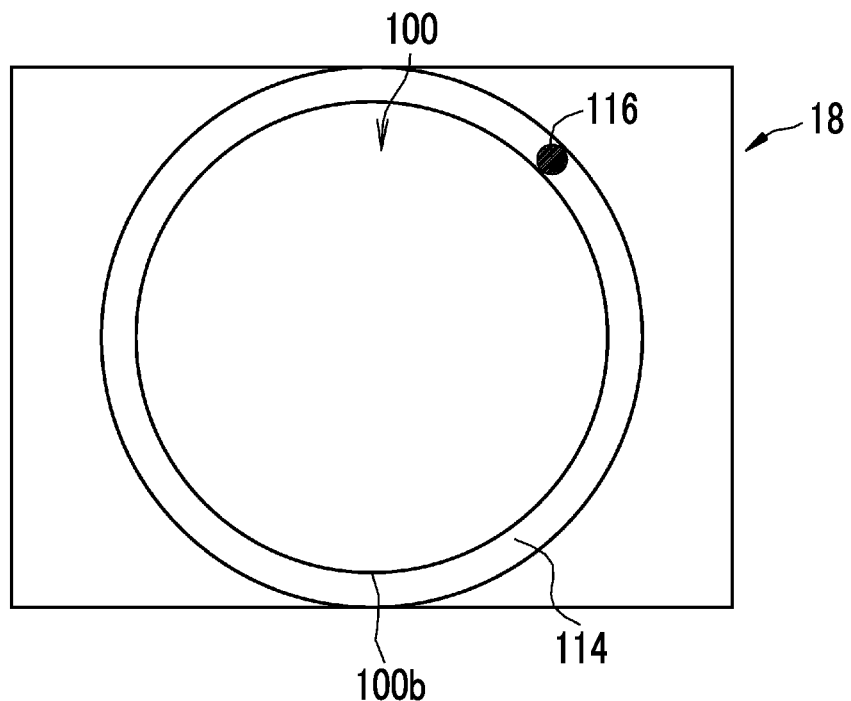
FIG. 11 is an image diagram of the monitor that displays a direct-viewing observation image and a detection index displayed in an index display region.

Further, as shown in FIG. 11, an index display region 114 (third display region) may be provided around a display region 100*b* for observation displaying the direct-viewing observation image 100, and a detection index 116 may be displayed in the index display region 114 in a state where the display region 100*b* for observation is maintained in a case where the region of interest is detected. The index display region 114 is formed so as to correspond to the shape of the display region 100*b* for observation. Accordingly, since the display region 100*b* for observation has a circular shape, the index display region 114 has an annular shape. In a case where the detection index 116 is to be displayed in the annular index display region 114, the detection index 116 is displayed at a portion corresponding to the position of the region of interest that is detected using the side-viewing observation image 102. Accordingly, even though an arrow is not used as the detection index 116 unlike the detection index 108 of FIG. 10, the position of the region of interest can be indicated. It is preferable that a ratio of a width to a height (screen aspect ratio) of the screen of the monitor 18 shown in FIG. 11 is 4:3.

Figure 12:
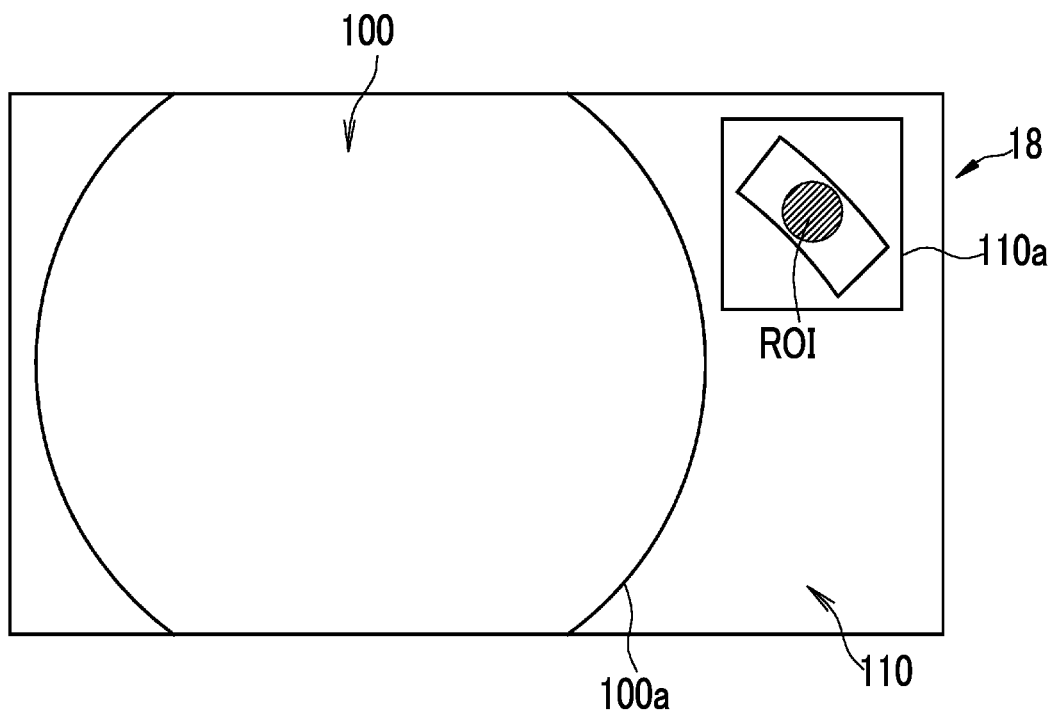
FIG. 12 is an image diagram of the monitor that displays a direct-viewing observation image and a region-of-interest image.

Furthermore, in a case where a region of interest is detected, a region-of-interest image including a portion of the side-viewing observation image 102 where the region of interest ROI is detected may be cut out and may be displayed on a sub-screen 110*a* displayed in the peripheral region 110 of the monitor 18 as shown in FIG. 12. Here, as described above, the display region 100*a* for observation, which displays the direct-viewing observation image, is maintained before and after the detection of the region of interest. It is preferable that a ratio of a width to a height (screen aspect ratio) of the screen of the monitor 18 shown in FIG. 12 is 16:9.

The region-of-interest image is formed of an image that is cut out of the side-viewing observation image 102 in an arc shape so as to include the image of the region of interest. Accordingly, the position of the region of interest can be grasped from the arc shape of the region-of-interest image. Further, since the region-of-interest image is an image obtained by cutting a part of the side-viewing observation image, which is not magnified electronically, out, the region-of-interest image has high quality and allows a user to clearly grasp the region of interest.

Figure 13A:
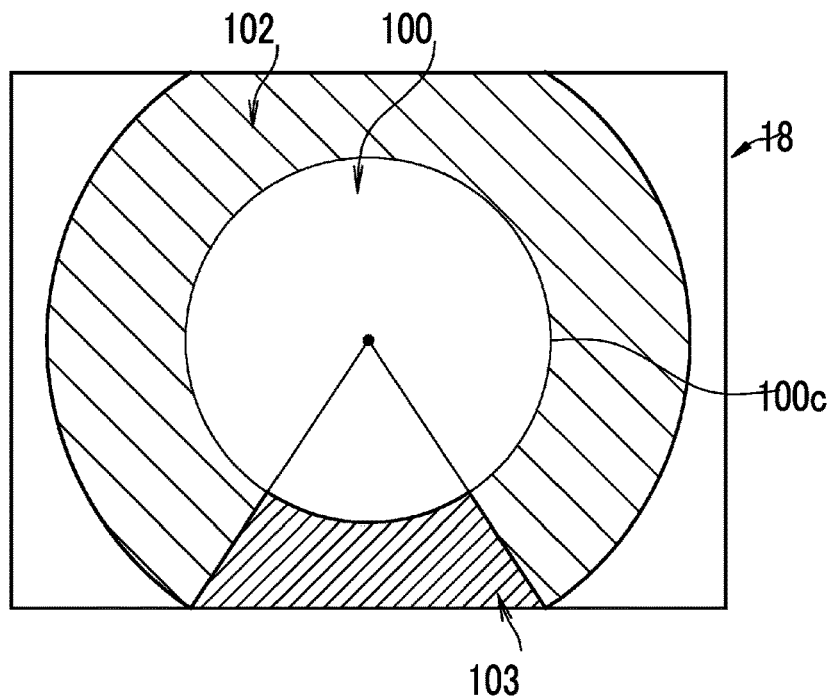
FIG. 13A is an image diagram of the monitor displaying a display aspect in a case where a region of interest is not detected.
Figure 13B:
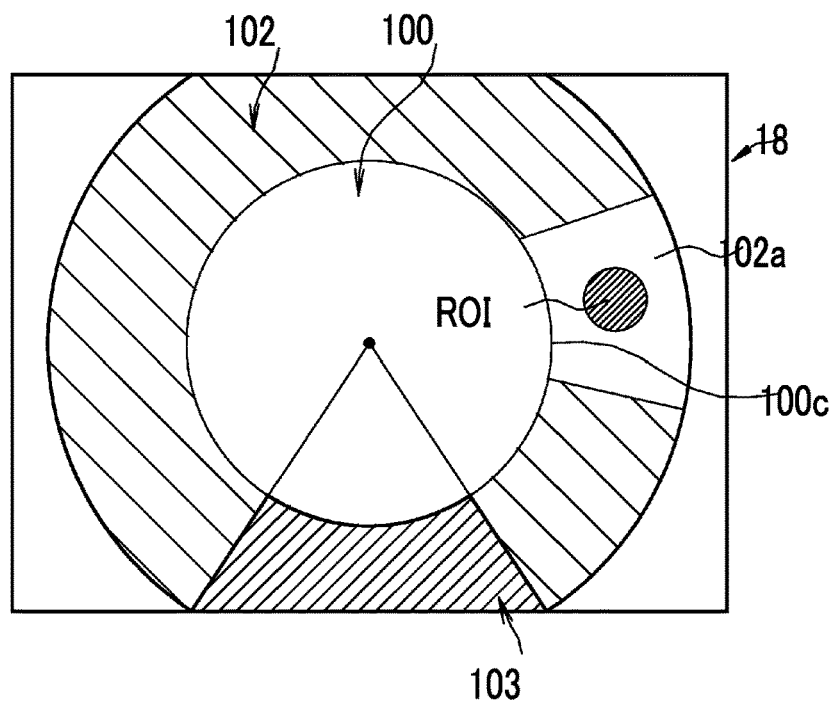
FIG. 13B is an image diagram of the monitor displaying a display aspect in a case where a region of interest is detected.

In the embodiment, only the electronically magnified direct-viewing observation image 100 is displayed on the monitor 18 in the specific display mode. However, as shown in FIG. 13A, the direct-viewing observation image 100 may be displayed on the monitor 18 without being magnified and displayed and the side-viewing observation image 102 may be adapted not to be displayed on the monitor 18 by mask processing (processing such as gray-out). Furthermore, in a case where the region of interest ROI is detected from the side-viewing observation image 102, as shown in FIG. 13B, the non-display of only a portion 102*a* where the region of interest ROI is detected is cancelled and the portion 102*a* is displayed on the monitor 18 (mask processing is cancelled) and the non-display of portions other than the portion where the region of interest is detected is maintained (mask processing is maintained). Even in FIG. 13A and FIG. 13B, as described above, a display region 100*c* for observation displaying the direct-viewing observation image 100 is maintained before and after the detection of the region of interest.

Figure 14:
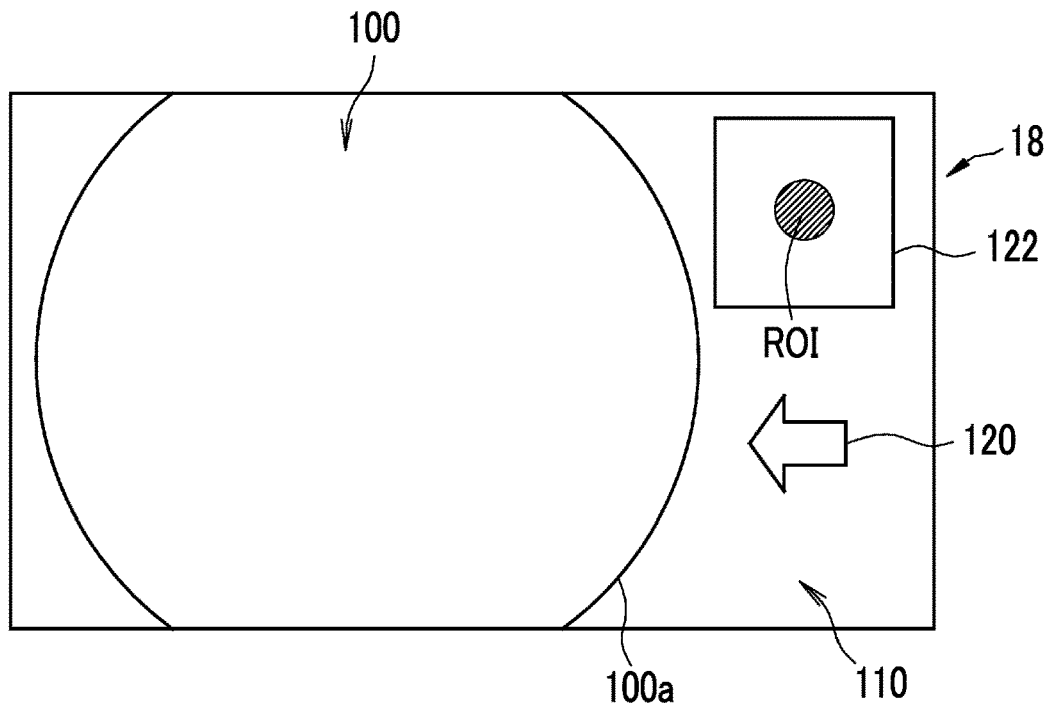
FIG. 14 is an image diagram of the monitor that displays a direct-viewing observation image, an arrow showing an image sensor having detected a region of interest, and the image of the region of interest.
Figure 15:
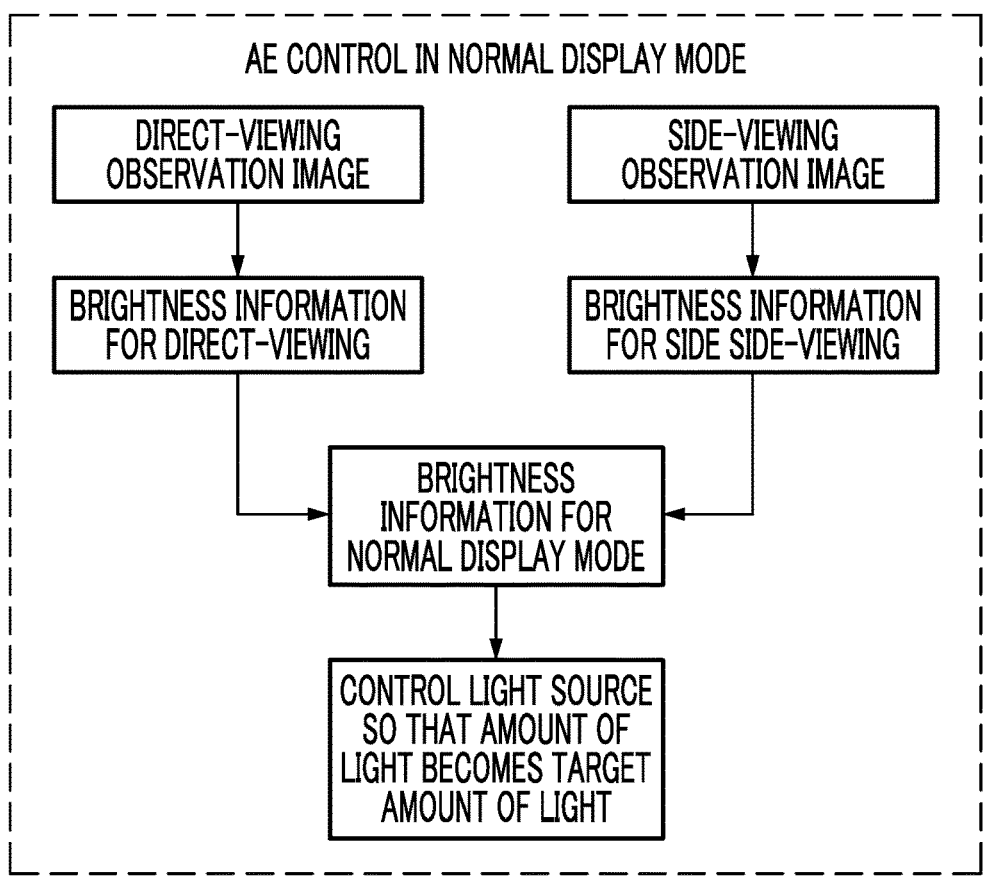
FIG. 15 is a diagram showing AE control in a normal display mode.
Figure 16:
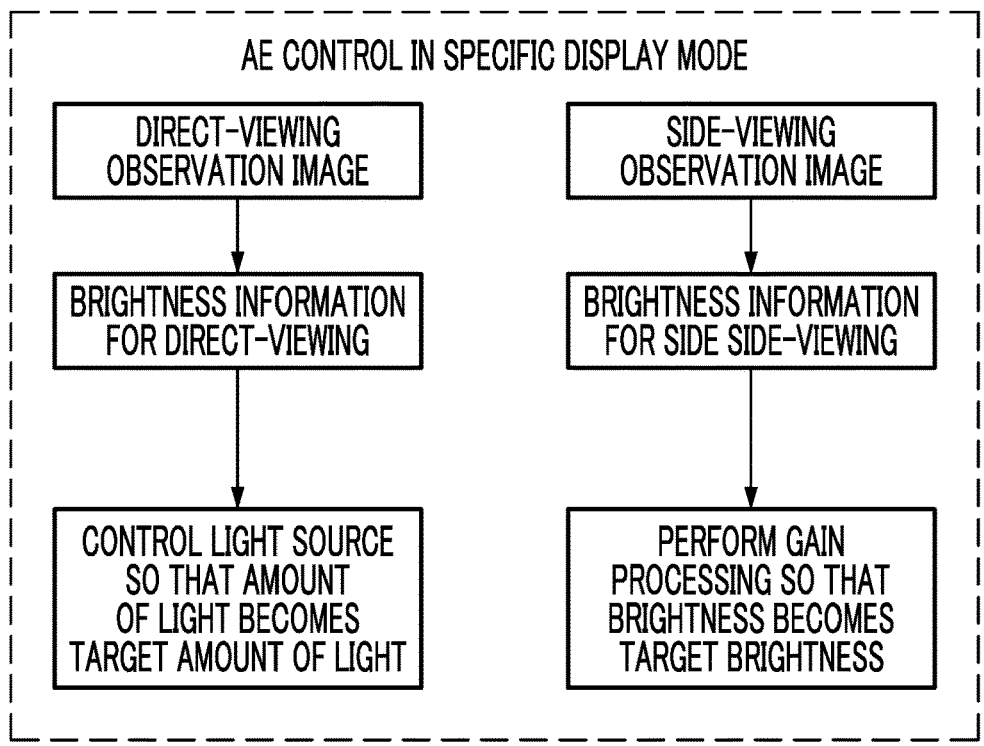
FIG. 16 is a diagram showing AE control in a specific display mode.

In the embodiment, both the direct-viewing observation image and the side-viewing observation image are acquired using one image sensor 66. However, the direct-viewing observation image and the side-viewing observation image may be acquired using different image sensors. For example, an image sensor for acquiring a left side-viewing observation image and an image sensor for acquiring a right side-viewing observation image may be provided in addition to the image sensor for acquiring a direct-viewing observation image. In this case, in a case where a region of interest is detected by the image sensor for acquiring a right side-viewing observation image, an arrow 120, which represents that the region of interest is detected by the image sensor for acquiring a right side-viewing observation image, and an image 122 of the region of interest ROI, which is acquired by the image sensor for acquiring a right side-viewing observation image, are displayed in the peripheral region 110 of the monitor 18 in addition to the direct-viewing observation image 100 as shown in FIG. 14. Even in FIG. 14, as described above, the display region 100*a* for observation displaying the direct-viewing observation image 100 is maintained before and after the detection of the region of interest. Further, it is preferable that a ratio of a width to a height (screen aspect ratio) of the screen of the monitor 18 shown in FIG. 12 is 16:9.

Next, AE control in the normal display mode and the specific display mode will be described. Since both the direct-viewing observation image and the side-viewing observation image are displayed on the monitor 18 in the normal display mode, it is preferable that the brightness of the direct-viewing observation image and the brightness of the side-viewing observation image are in balance. In the normal display mode, the control unit 96 calculates brightness information for direct-viewing from the direct-viewing observation image and calculates brightness information for side-viewing from the side-viewing observation image by a brightness information calculation unit 96*a* (see FIG. 6). Further, the control unit 96 calculates brightness information for a normal display mode that is obtained on the basis of the brightness information for direct-viewing and the brightness information for side-viewing, and sends the calculated brightness information for a normal display mode to the light source control unit 92. It is preferable that the brightness information for a normal display mode is, for example, an average of the brightness information for direct-viewing and the brightness information for side-viewing. The light source control unit 92 controls the light source 91 on the basis of the brightness information for a normal display mode so that the amount of light becomes a target amount of light.

In a case where the light source is controlled on the basis of either brightness information in a state where brightness in the direct-viewing direction is different from brightness in the side-viewing direction, it is difficult to achieve a balance in terms of brightness. For example, in a case where the amount of illumination light is increased on the basis of brightness information in the side-viewing direction in a state where a region in the side-viewing direction is dark, a region in the direct-viewing direction becomes excessively bright in the case of a certain shape of an organ. For this reason, it is difficult to achieve a balance in terms of brightness. Accordingly, in this embodiment, the light source is controlled using an average of the brightness information in the direct-viewing direction and the brightness information in the side-viewing direction. As a result, it is easy to achieve a balance in terms of brightness.

On the other hand, since only the direct-viewing observation image is displayed on the monitor 18 in the specific display mode, the brightness of the direct-viewing observation image and the brightness of the side-viewing observation image may be different from each other. Accordingly, even in the specific display mode, the control unit 96 calculates brightness information for direct-viewing from the direct-viewing observation image, and calculates brightness information for side-viewing (brightness information for an image not to be displayed) from the side-viewing observation image. The control unit 96 sends the brightness information for direct-viewing to the light source control unit 92. The light source control unit 92 controls the light source 91 on the basis of the brightness information for direct-viewing so that the amount of light becomes a target amount of light. On the other hand, the control unit 96 sends the brightness information for side-viewing to the image processing unit 99. The image processing unit 99 performs gain processing on the side-viewing observation image on the basis of the brightness information for side-viewing so that brightness becomes target brightness. The side-viewing observation image on which the gain processing has been performed is used to detect a region of interest. The side-viewing observation image is not displayed on the monitor 18 in the specific display mode as described above. Accordingly, even though noise is increased due to the gain processing, there is no problem as long as the increased noise allows the structure or color of a lesion to be recognized, that is, does not affect the detection of a region of interest.

Figure 17:
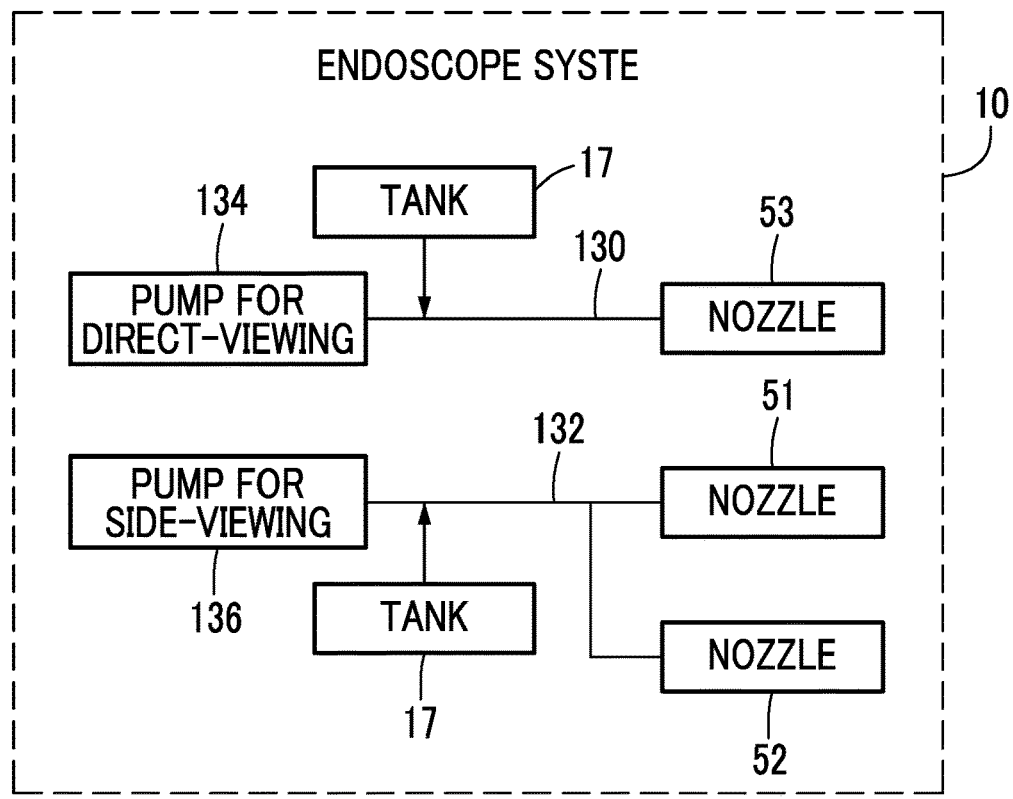

An operation, which is related to the cleaning of the direct-viewing observation window 41A or the side-viewing observation window 42A to be performed in the normal display mode, and an operation, which is related to the cleaning of the direct-viewing observation window 41A or the side-viewing observation window 42A to be performed in the specific display mode, will be described. As shown in FIG. 17, a fluid feed line 130 for direct-viewing, which feeds cleaning fluid to the nozzle 53 for cleaning the direct-viewing observation window (a nozzle for direct-viewing) from the tank 17, and a fluid feed line 132 for side-viewing, which feeds cleaning fluid to the nozzles 51 and 52 for cleaning the side-viewing observation window (a nozzle for side-viewing) from the tank 17, are separately provided in the endoscope system 10. Further, a pump 134 for direct-viewing, which sucks cleaning fluid from the tank 17 and feeds the cleaning fluid to the fluid feed line 130 for direct-viewing, and a pump 136 for side-viewing, which sucks cleaning fluid from the tank 17 and feeds the cleaning fluid to the fluid feed line 132 for side-viewing, are provided in the endoscope system 10.

Figure 18:
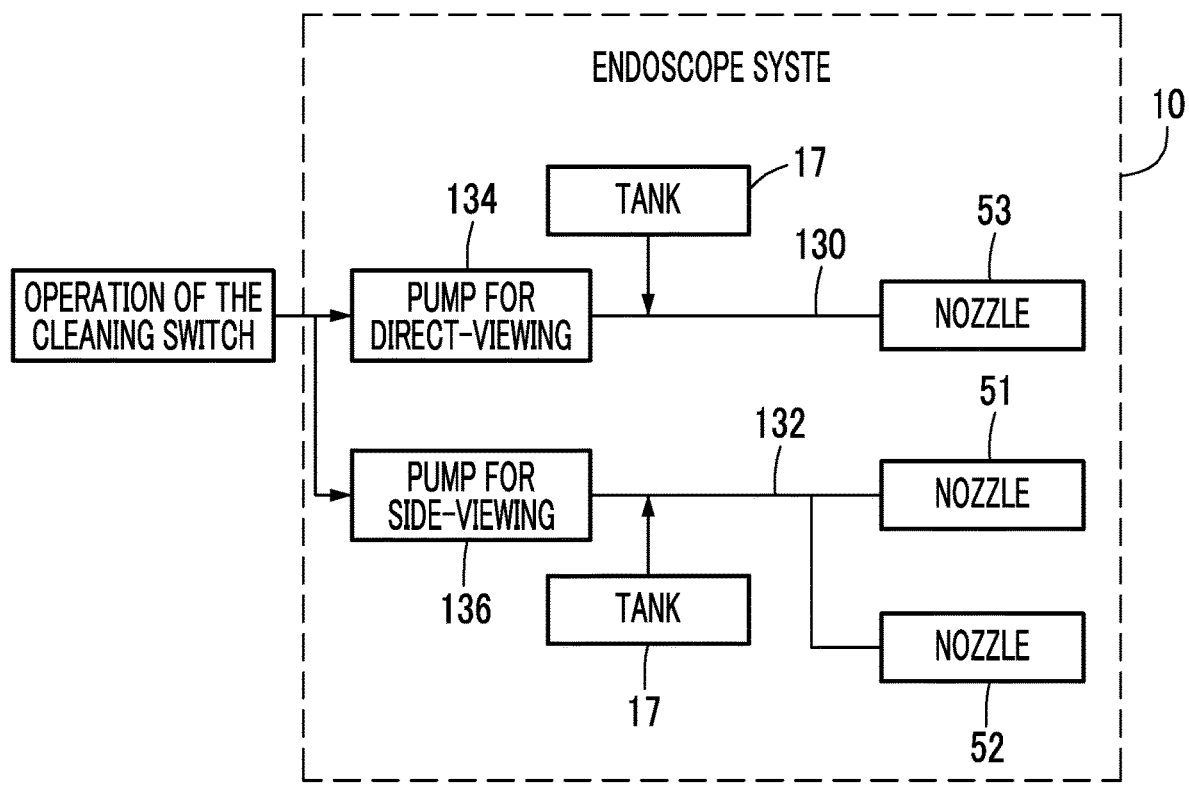
FIG. 18 is a diagram showing an operation related to the cleaning of a direct-viewing observation window or a side-viewing observation window that is performed in a case where the endoscope system is set to the normal display mode.

In a case where the endoscope system 10 is set to the normal display mode, the pump 134 for direct-viewing and the pump 136 for side-viewing are driven by the operation of the cleaning switch 13a as shown in FIG. 18. Accordingly, cleaning fluid sucked from the tank 17 is ejected to the direct-viewing observation window 41A through the fluid feed line 130 for direct-viewing and the nozzle 53. Further, cleaning fluid sucked from the tank 17 is ejected to the side-viewing observation window 42A through the fluid feed line 132 for side-viewing and the nozzles 51 and 52.

Figure 19:
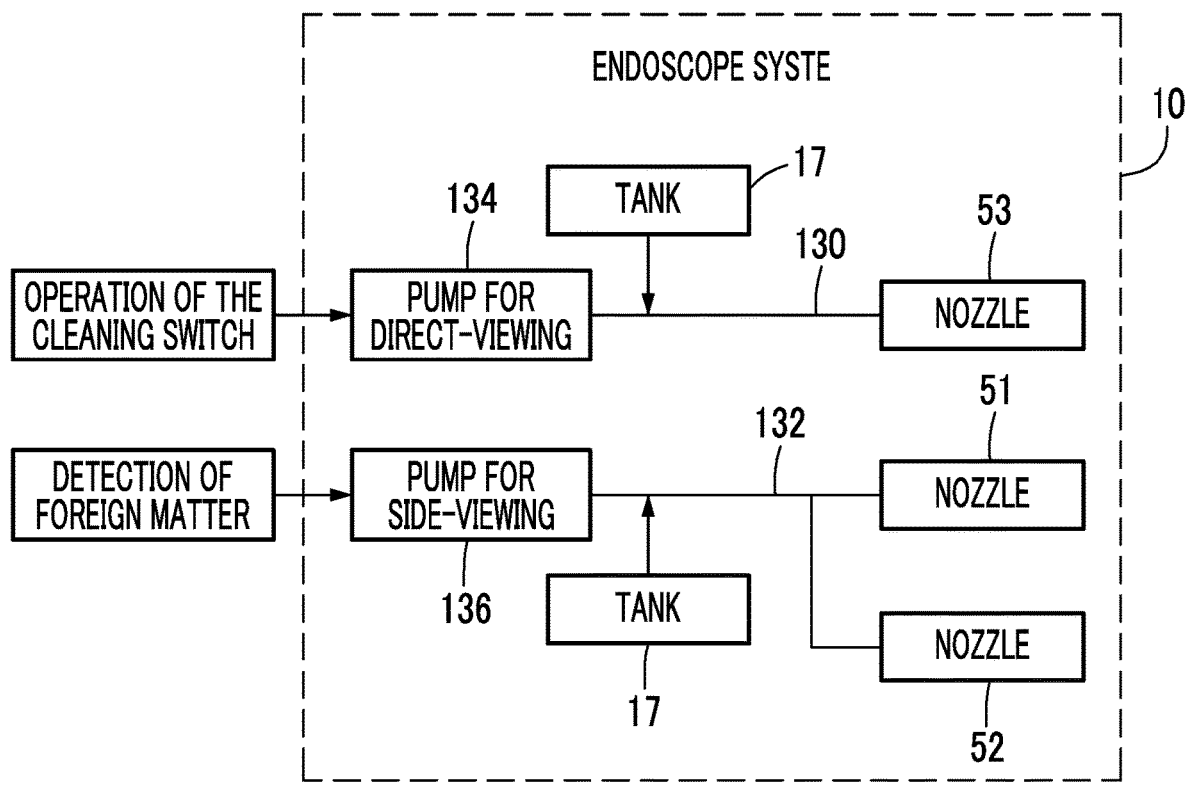
FIG. 19 is a diagram showing an operation related to the cleaning of the direct-viewing observation window or the side-viewing observation window that is performed in a case where the endoscope system is set to the specific display mode.

In a case where the endoscope system 10 is set to the specific display mode, only the pump 134 for direct-viewing is driven by the operation of the cleaning switch 13a as shown in FIG. 19. Accordingly, cleaning fluid sucked from the tank 17 is ejected to the direct-viewing observation window 41A through the fluid feed line 130 for direct-viewing and the nozzle 53. On the other hand, in regard to the drive of the pump 136 for side-viewing, the pump 136 for side-viewing is driven in a case where a foreign matter is detected by the foreign matter detection unit 99b of the image processing unit 99. Accordingly, cleaning fluid sucked from the tank 17 is ejected to the side-viewing observation window 42A through the fluid feed line 132 for side-viewing and the nozzles 51 and 52. Since the side-viewing observation image is not displayed on the monitor 18 in the specific display mode, observation performed by a user is not affected even though cleaning fluid is ejected to the side-viewing observation window 42A at any timing.

Furthermore, since the fluid feed line 130 for direct-viewing and the fluid feed line 132 for side-viewing are independent of each other, cleaning fluid to be used to clean the side-viewing observation window 42A is not ejected to the direct-viewing observation window 41A. Accordingly, a user can continue to observe an object without interrupting examination, and the number of times of operating the cleaning switch 13a is also reduced since a user operates the cleaning switch 13a only in a case where the direct-viewing observation window 41A is dirty. As a result, user's stress can be reduced. In the specific display mode, the cleaning of the side-viewing observation window 42A is automatically performed on the basis of the detection of a foreign matter. However, the side-viewing observation window 42A may be cleaned at a fixed timing regardless of the detection of a foreign matter.

In the embodiment, the hardware structures of processing units, which perform various kinds of processing, such as the control unit 96, the image acquisition unit 97, the display control unit 98, and the image processing unit 99 (the region-of-interest detection unit 99a and the foreign matter detection unit 99b), are various processors to be described below. The various processors include: a central processing unit (CPU) that is a general-purpose processor functioning as various processing units by executing software (program); a graphical processing unit (GPU); a programmable logic device (PLD), which is a processor of which circuit configuration can be changed after manufacture, such as a field programmable gate array (FPGA); a dedicated electrical circuit that is a processor having circuit configuration designed exclusively to perform various kinds of processing; and the like.

One processing unit may be formed of one of these various processors, or may be formed of a combination of two or more same kind or different kinds of processors (for example, a plurality of FPGAs, a combination of a CPU and an FPGA, a combination of a CPU and a GPU, or the like). Further, a plurality of processing units may be formed of one processor. As an example where a plurality of processing units are formed of one processor, first, there is an aspect where one processor is formed of a combination of one or more CPUs and software as typified by a computer, such as a client or a server, and functions as a plurality of processing units. Second, there is an aspect where a processor fulfilling the functions of the entire system, which includes a plurality of processing units, by one integrated circuit (IC) chip as typified by System On Chip (SoC) or the like is used. In this way, various processing units are formed using one or more of the above-mentioned various processors as hardware structures.

In addition, the hardware structures of these various processors are more specifically electrical circuitry where circuit elements, such as semiconductor elements, are combined.

EXPLANATION OF REFERENCES

10: endoscope system
11: universal cord
12: endoscope
12a: insertion part
12b: operation part
12c: bendable part
12d: distal end part
12e: angle knob
13a: cleaning switch
13b: mode changeover switch
14: light source device
16: processor device
17: tank
18: monitor
19: user interface
21: distal end face
31: first protruding portion
32: second protruding portion
41: direct-viewing observation unit
41A: direct-viewing observation window
42: side-viewing observation unit
42A: side-viewing observation window
43: direct-viewing/side-viewing illumination unit
43: side-viewing illumination unit
43A: direct-viewing/side-viewing illumination window
51, 52, 53: nozzle
54: direct-viewing illumination unit
54A: direct-viewing illumination window
61: image pickup lens
62: front group lens
62: front group lens
63: mirror lens
64: rear group lens
66: image sensor
66a: direct-viewing image pickup region
66b: side-viewing image pickup region
67: cover glass
71: light guide
72: reflective member
73: filling member
77: light guide
78: illumination lens
81: direct-viewing illumination unit
81A: direct-viewing illumination window
82: forceps port
84: light guide
91: light source
92: light source control unit
93: light guide
96: control unit
96a: brightness information calculation unit
97: image acquisition unit
98: display control unit
99: image processing unit
99: region-of-interest detection unit
99a: region-of-interest detection unit
99b: foreign matter detection unit
100: direct-viewing observation image
100a: display region for observation
100b: display region for observation
100c: display region for observation
102: side-viewing observation image
102a: portion
103: blind spot portion
105: image
108: detection index
110: peripheral region
110a: sub-screen
114: index display region
116: detection index
120: arrow
122: image
130: fluid feed line for direct-viewing
132: fluid feed line for side-viewing
134: pump for direct-viewing
136: pump for side-viewing
ROI: region of interest

What is claimed is:

1. An endoscope system comprising:

an endoscope that includes an insertion part to be inserted into an object to be observed, a direct-viewing observation unit having a field of view in a distal end direction of the insertion part, and a side-viewing observation unit having a field of view in a lateral direction of the insertion part;

an image acquisition unit that acquires a direct-viewing observation image by the direct-viewing observation unit and acquires a side-viewing observation image by the side-viewing observation unit;

a display control unit that displays one of the direct-viewing observation image and the side-viewing observation image on a display unit as an image to be displayed and does not display the other thereof as an image not to be displayed; and a region-of-interest detection unit that detects a region of interest by using the image to be displayed or the image not to be displayed, wherein the display control unit maintains a first display region, which displays the image to be displayed, of the display unit regardless of whether or not the region of interest is detected by the region-of-interest detection unit.

2. The endoscope system according to claim 1, wherein the display control unit displays a detection index, which indicates detection of the region of interest, on the display unit in a case where the region of interest is detected.

3. The endoscope system according to claim 2,
wherein the detection index indicates a position of the region of interest.

4. The endoscope system according to claim 2,
wherein the detection index is displayed in a second display region that is provided at a position different from a position of the first display region.

5. The endoscope system according to claim 2,
wherein the detection index is displayed in a third display region that is provided around the first display region and is formed so as to correspond to a shape of the first display region.

6. The endoscope system according to claim 5,
wherein the third display region has an annular shape.

7. The endoscope system according to claim 2,
wherein a color or a shape of the detection index is changed depending on a size or the kind of the region of interest.

8. The endoscope system according to claim 1,
wherein the display control unit displays a region-of-interest image, which includes a portion of the image not to be displayed where the region of interest is detected, on the display unit in a case where the region of interest is detected.

9. The endoscope system according to claim 1,
wherein the display control unit cancels the non-display of a portion where the region of interest is detected and displays the portion on the display unit in a case where the region of interest is detected.

10. The endoscope system according to claim 1,
wherein the display control unit electronically magnifies the image to be displayed and displays the image to be displayed on the display unit.

11. The endoscope system according to claim 1,
wherein the image acquisition unit acquires the direct-viewing observation image and the side-viewing observation image from an image that is obtained from one image sensor.

12. The endoscope system according to claim 1,
wherein the direct-viewing observation image is acquired from an image sensor for acquiring a direct-viewing observation image, and the side-viewing observation image is acquired from an image sensor for acquiring a side-viewing observation image different from the image sensor for acquiring a direct-viewing observation image.

13. The endoscope system according to claim 1, further comprising:
a mode changeover switch that switches a normal display mode where both the direct-viewing observation image and the side-viewing observation image are displayed on the display unit and a specific display mode where the image to be displayed is displayed on the display unit and the image not to be displayed is not displayed.

14. The endoscope system according to claim 1, further comprising:
a brightness information acquisition unit that acquires brightness information for an image not to be displayed from the image not to be displayed,
wherein gain processing for obtaining target brightness is performed on the image not to be displayed on the basis of the brightness information for an image not to be displayed.

15. The endoscope system according to claim 1, further comprising:
an image processing unit that performs image processing, which is different for each frame, on the image not to be displayed.

16. The endoscope system according to claim 1,
wherein the direct-viewing observation unit is provided with a direct-viewing observation window and the side-viewing observation unit is provided with a side-viewing observation window,
a fluid feed line for side-viewing that feeds cleaning fluid to a nozzle for side-viewing to be used for cleaning the side-viewing observation window is provided separately from a fluid feed line for direct-viewing that feeds the cleaning fluid to a nozzle for direct-viewing to be used for cleaning the direct-viewing observation window, and
the cleaning fluid is automatically ejected to the side-viewing observation window through the fluid feed line for side-viewing and the nozzle for side-viewing in a case where a foreign matter is detected in the image not to be displayed.

* * * * *